(12) United States Patent
Elomari

(10) Patent No.: US 7,083,714 B2
(45) Date of Patent: Aug. 1, 2006

(54) HYDROCARBON CONVERSION USING MOLECULAR SIEVE SSZ-65

(75) Inventor: Saleh Elomari, Fairfield, CA (US)

(73) Assignee: Chevron U.S.A. Inc., San Ramon, CA (US)

( * ) Notice: Subject to any disclaimer, the term of this patent is extended or adjusted under 35 U.S.C. 154(b) by 0 days.

(21) Appl. No.: 10/956,313

(22) Filed: Sep. 30, 2004

(65) Prior Publication Data

US 2005/0040074 A1    Feb. 24, 2005

Related U.S. Application Data

(63) Continuation-in-part of application No. 10/401,618, filed on Mar. 26, 2003, now abandoned.

(51) Int. Cl.
| C10G 47/02 | (2006.01) |
| C10C 11/02 | (2006.01) |
| C10C 35/04 | (2006.01) |
| C07C 2/68  | (2006.01) |

(52) U.S. Cl. ............. 208/111.01; 208/134; 208/120.01; 585/467; 585/475; 585/407; 585/481; 585/639; 585/502

(58) Field of Classification Search ........... 208/111.01, 208/134, 120.01; 585/467, 475, 407, 481, 585/639, 502

See application file for complete search history.

(56) References Cited

U.S. PATENT DOCUMENTS

| 3,140,249 A | 7/1964 | Plank et al. |
| 3,140,251 A | 7/1964 | Plank et al. |
| 3,140,253 A | 7/1964 | Plank et al. |
| 3,894,107 A | 7/1975 | Butler et al. |
| 3,960,978 A | 6/1976 | Givens et al. |
| 4,181,598 A | 1/1980 | Gillespie et al. |
| 4,559,315 A | 12/1985 | Chang et al. |
| 4,734,537 A | 3/1988 | Devries et al. |
| 4,910,006 A | 3/1990 | Zones et al. |
| 4,921,594 A | 5/1990 | Miller |
| 4,939,311 A | 7/1990 | Washecheck et al. |
| 4,962,261 A | 10/1990 | Abrevaya et al. |
| 5,095,161 A | 3/1992 | Abrevaya et al. |
| 5,105,044 A | 4/1992 | Han et al. |
| 5,105,046 A | 4/1992 | Washecheck |
| 5,149,421 A | 9/1992 | Miller |
| 5,225,179 A | 7/1993 | Zones et al. |
| 5,238,898 A | 8/1993 | Han et al. |
| 5,316,753 A | 5/1994 | Nakagawa |
| 5,321,185 A | 6/1994 | van der Vaart |
| 5,336,825 A | 8/1994 | Choudhary et al. |

OTHER PUBLICATIONS

Christopher W. Jones et al., Synthesis of Hydrophobic Molecular Sieves by Hydrothermal Treatment with Acetic Acid, 2001 American Chemical Society, Chem Matter, 2001, 1041-1050, 13, Division of Chemistry and Chemical Engineering, California Institute of Technology, Pasadena, California.*

Akira Saito et al., Argon porosimetry of selected molecular sieves: experiments and examination of the adapted Horvath-Kawazoe model, Microporous Materials, 1995, 531-542, 3, Elsevier Science B.V.*

B.C. Lippens et al., Studies on Pore Systems in Catalysts V. the t method, Journal of Catalysis, 1965, 319-323, 4, From the Department of Chemical Technology. Technological University of Delft, The Netherlands.*

* cited by examiner

Primary Examiner—Tam M. Nguyen
(74) Attorney, Agent, or Firm—Richard J. Sheridan

(57) ABSTRACT

The present invention relates to new crystalline molecular sieve SSZ-65 prepared using 1-[1-(4-chlorophenyl)-cyclopropylmethyl]-1-ethyl-pyrrolidinium or 1-ethyl-1-(1-phenyl-cyclopropylmethyl)-pyrrolidinium cation as a structure-directing agent, methods for synthesizing SSZ-65 and processes employing SSZ-65 in a catalyst.

54 Claims, No Drawings

HYDROCARBON CONVERSION USING MOLECULAR SIEVE SSZ-65

This application is a continuation-in-part of application Ser. No. 10/401,618, filed Mar. 26, 2003 now abandoned.

BACKGROUND OF THE INVENTION

1. Field of the Invention

The present invention relates to new crystalline molecular sieve SSZ-65, a method for preparing SSZ-65 using a 1-[1-(4-chlorophenyl)-cyclopropylmethyl]-1-ethyl-pyrrolidinium or 1-ethyl-1-(1-phenyl-cyclopropylmethyl)-pyrrolidinium cation as a structure directing agent and the use of SSZ-65 in catalysts for, e.g., hydrocarbon conversion reactions.

2. State of the Art

Because of their unique sieving characteristics, as well as their catalytic properties, crystalline molecular sieves and zeolites are especially useful in applications such as hydrocarbon conversion, gas drying and separation. Although many different crystalline molecular sieves have been disclosed, there is a continuing need for new zeolites with desirable properties for gas separation and drying, hydrocarbon and chemical conversions, and other applications. New zeolites may contain novel internal pore architectures, providing enhanced selectivities in these processes.

Crystalline aluminosilicates are usually prepared from aqueous reaction mixtures containing alkali or alkaline earth metal oxides, silica, and alumina. Crystalline borosilicates are usually prepared under similar reaction conditions except that boron is used in place of aluminum. By varying the synthesis conditions and the composition of the reaction mixture, different zeolites can often be formed.

SUMMARY OF THE INVENTION

The present invention is directed to a family of crystalline molecular sieves with unique properties, referred to herein as "molecular sieve SSZ-65" or simply "SSZ-65". Preferably, SSZ-65 is obtained in its silicate, aluminosilicate, titanosilicate, germanosilicate, vanadosilicate or borosilicate form. The term "silicate" refers to a molecular sieve having a high mole ratio of silicon oxide relative to aluminum oxide, preferably a mole ratio greater than 100, including molecular sieves comprised entirely of silicon oxide. As used herein, the term "aluminosilicate" refers to a molecular sieve containing both aluminum oxide and silicon oxide and the term "borosilicate" refers to a molecular sieve containing oxides of both boron and silicon.

In accordance with the present invention there is provided a process for converting hydrocarbons comprising contacting a hydrocarbonaceous feed at hydrocarbon converting conditions with a catalyst comprising the zeolite of this invention. The zeolite may be predominantly in the hydrogen form. It may also be substantially free of acidity.

Further provided by the present invention is a hydrocracking process comprising contacting a hydrocarbon feedstock under hydrocracking conditions with a catalyst comprising the zeolite of this invention, preferably predominantly in the hydrogen form.

This invention also includes a dewaxing process comprising contacting a hydrocarbon feedstock under dewaxing conditions with a catalyst comprising the zeolite of this invention, preferably predominantly in the hydrogen form.

The present invention also includes a process for improving the viscosity index of a dewaxed product of waxy hydrocarbon feeds comprising contacting the waxy hydrocarbon feed under isomerization dewaxing conditions with a catalyst comprising the zeolite of this invention, preferably predominantly in the hydrogen form.

The present invention further includes a process for producing a $C_{20+}$ lube oil from a $C_{20+}$ olefin feed comprising isomerizing said olefin feed under isomerization conditions over a catalyst comprising the zeolite of this invention. The zeolite may be predominantly in the hydrogen form. The catalyst may contain at least one Group VIII metal.

In accordance with this invention, there is also provided a process for catalytically dewaxing a hydrocarbon oil feedstock boiling above about 350° F. (177° C.) and containing straight chain and slightly branched chain hydrocarbons comprising contacting said hydrocarbon oil feedstock in the presence of added hydrogen gas at a hydrogen pressure of about 15–3000 psi (0.103–20.7 MPa) with a catalyst comprising the zeolite of this invention, preferably predominantly in the hydrogen form. The catalyst may contain at least one Group VIII metal. The catalyst may be a layered catalyst comprising a first layer comprising the zeolite of this invention, and a second layer comprising an aluminosilicate zeolite which is more shape selective than the zeolite of said first layer. The first layer may contain at least one Group VIII metal.

Also included in the present invention is a process for preparing a lubricating oil which comprises hydrocracking in a hydrocracking zone a hydrocarbonaceous feedstock to obtain an effluent comprising a hydrocracked oil, and catalytically dewaxing said effluent comprising hydrocracked oil at a temperature of at least about 400° F. (204° C.) and at a pressure of from about 15 psig to about 3000 psig (0.103–20.7 MPa gauge)in the presence of added hydrogen gas with a catalyst comprising the zeolite of this invention. The zeolite may be predominantly in the hydrogen form. The catalyst may contain at least one Group VIII metal.

Further included in this invention is a process for isomerization dewaxing a raffinate comprising contacting said raffinate in the presence of added hydrogen with a catalyst comprising the zeolite of this invention. The raffinate may be bright stock, and the zeolite may be predominantly in the hydrogen form. The catalyst may contain at least one Group VIII metal.

Also included in this invention is a process for increasing the octane of a hydrocarbon feedstock to produce a product having an increased aromatics content comprising contacting a hydrocarbonaceous feedstock which comprises normal and slightly branched hydrocarbons having a boiling range above about 40° C. and less than about 200° C., under aromatic conversion conditions with a catalyst comprising the zeolite of this invention made substantially free of acidity by neutralizing said zeolite with a basic metal. Also provided in this invention is such a process wherein the zeolite contains a Group VIII metal component.

Also provided by the present invention is a catalytic cracking process comprising contacting a hydrocarbon feedstock in a reaction zone under catalytic cracking conditions in the absence of added hydrogen with a catalyst comprising the zeolite of this invention, preferably predominantly in the hydrogen form. Also included in this invention is such a catalytic cracking process wherein the catalyst additionally comprises a large pore crystalline cracking component.

This invention further provides an isomerization process for isomerizing $C_4$ to $C_7$ hydrocarbons, comprising contacting a feed having normal and slightly branched $C_4$ to $C_7$ hydrocarbons under isomerizing conditions with a catalyst comprising the zeolite of this invention, preferably predominantly in the hydrogen form. The zeolite may be impregnated with at least one Group VIII metal, preferably platinum. The catalyst may be calcined in a steam/air mixture at an elevated temperature after impregnation of the Group VIII metal.

Also provided by the present invention is a process for alkylating an aromatic hydrocarbon which comprises contacting under alkylation conditions at least a molar excess of an aromatic hydrocarbon with a $C_2$ to $C_{20}$ olefin under at least partial liquid phase conditions and in the presence of a catalyst comprising the zeolite of this invention, preferably predominantly in the hydrogen form. The olefin may be a $C_2$ to $C_4$ olefin, and the aromatic hydrocarbon and olefin may be present in a molar ratio of about 4:1 to about 20:1, respectively. The aromatic hydrocarbon may be selected from the group consisting of benzene, toluene, ethylbenzene, xylene, naphthalene, naphthalene derivatives, dimethylnaphthalene or mixtures thereof.

Further provided in accordance with this invention is a process for transalkylating an aromatic hydrocarbon which comprises contacting under transalkylating conditions an aromatic hydrocarbon with a polyalkyl aromatic hydrocarbon under at least partial liquid phase conditions and in the presence of a catalyst comprising the zeolite of this invention, preferably predominantly in the hydrogen form. The aromatic hydrocarbon and the polyalkyl aromatic hydrocarbon may be present in a molar ratio of from about 1:1 to about 25:1, respectively.

The aromatic hydrocarbon may be selected from the group consisting of benzene, toluene, ethylbenzene, xylene, or mixtures thereof, and the polyalkyl aromatic hydrocarbon may be a dialkylbenzene.

Further provided by this invention is a process to convert paraffins to aromatics which comprises contacting paraffins under conditions which cause paraffins to convert to aromatics with a catalyst comprising the zeolite of this invention, said catalyst comprising gallium, zinc, or a compound of gallium or zinc.

In accordance with this invention there is also provided a process for isomerizing olefins comprising contacting said olefin under conditions which cause isomerization of the olefin with a catalyst comprising the zeolite of this invention.

Further provided in accordance with this invention is a process for isomerizing an isomerization feed comprising an aromatic $C_8$ stream of xylene isomers or mixtures of xylene isomers and ethylbenzene, wherein a more nearly equilibrium ratio of ortho-, meta- and para-xylenes is obtained, said process comprising contacting said feed under isomerization conditions with a catalyst comprising the zeolite of this invention.

The present invention further provides a process for oligomerizing olefins comprising contacting an olefin feed under oligomerization conditions with a catalyst comprising the zeolite of this invention.

This invention also provides a process for converting oxygenated hydrocarbons comprising contacting said oxygenated hydrocarbon with a catalyst comprising the zeolite of this invention under conditions to produce liquid products. The oxygenated hydrocarbon may be a lower alcohol.

Further provided in accordance with the present invention is a process for the production of higher molecular weight hydrocarbons from lower molecular weight hydrocarbons comprising the steps of:

(a) introducing into a reaction zone a lower molecular weight hydrocarbon-containing gas and contacting said gas in said zone under $C_{2+}$ hydrocarbon synthesis conditions with the catalyst and a metal or metal compound capable of converting the lower molecular weight hydrocarbon to a higher molecular weight hydrocarbon; and (b) withdrawing from said reaction zone a higher molecular weight hydrocarbon-containing stream.

DETAILED DESCRIPTION OF THE INVENTION

The present invention comprises a family of crystalline, large pore molecular sieves designated herein "molecular sieve SSZ-65" or simply "SSZ-65". As used herein, the term "large pore" means having an average pore size diameter greater than about 6.0 Angstroms, preferably from about 6.5 Angstroms to about 7.5 Angstroms.

In preparing SSZ-65, a 1-[1-(4-chlorophenyl)-cyclopropylmethyl]-1-ethyl-pyrrolidinium or 1-ethyl-1-(1-phenyl-cyclopropylmethyl)-pyrrolidinium cation is used as a structure directing agent ("SDA"), also known as a crystallization template. The SDA's useful for making SSZ-65 have the following structures:

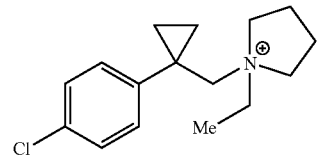

1-[1-(4-Chloro-phenyl)-cyclopropylmethyl]-1-ethyl-pyrrolidinium

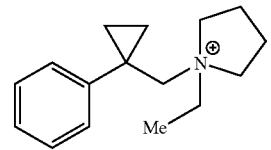

1-Ethyl-1-(1-phenyl-cyclopropylmethyl)-pyrrolidinium

The SDA cation is associated with an anion ($X^-$) which may be any anion that is not detrimental to the formation of the zeolite. Representative anions include halogen, e.g., fluoride, chloride, bromide and iodide, hydroxide, acetate, sulfate, tetrafluoroborate, carboxylate, and the like. Hydroxide is the most preferred anion.

In general, SSZ-65 is prepared by contacting an active source of one or more oxides selected from the group consisting of monovalent element oxides, divalent element oxides, trivalent element oxides, tetravalent element oxides and/or pentavalent elements with the 1-[1-(4-chlorophenyl)-cyclopropylmethyl]-1-ethyl-pyrrolidinium or 1-ethyl-1-(1-phenyl-cyclopropylmethyl)-pyrrolidinium cation SDA.

SSZ-65 is prepared from a reaction mixture having the composition shown in Table A below.

TABLE A

| | Reaction Mixture | |
|---|---|---|
| | Typical | Preferred |
| $YO_2/W_aO_b$ | >15 | 30–70 |
| $OH^-/YO_2$ | 0.10–0.50 | 0.20–0.30 |
| $Q/YO_2$ | 0.05–0.50 | 0.10–0.20 |
| $M_{2/n}/YO_2$ | 0.02–0.40 | 0.10–0.25 |
| $H_2O/YO_2$ | 30–80 | 35–45 | where Y is silicon, germanium or a mixture thereof; W is aluminum, gallium, iron, boron, titanium, indium, vanadium or mixtures thereof, a is 1 or 2, b is 2 when a is 1 (i.e., W is tetravalent) and b is 3 when a is 2 (i.e., W is trivalent), M is an alkali metal cation, alkaline earth metal cation or mixtures thereof; n is the valence of M (i.e., 1 or 2); and Q is a 1-[1-(4-chlorophenyl)-cyclopropylmethyl]-1-ethyl-pyrrolidinium or 1-ethyl-1-(1-phenyl-cyclopropylmethyl)-pyrrolidinium cation.

In practice, SSZ-65 is prepared by a process comprising:
(a) preparing an aqueous solution containing sources of at least one oxide capable of forming a crystalline molecular sieve and a 1-[1-(4-chlorophenyl)-cyclopropylmethyl]-1-ethyl-pyrrolidinium or 1-ethyl-1-(1-phenyl-cyclopropylmethyl)-pyrrolidinium cation having an anionic counterion which is not detrimental to the formation of SSZ-65;
(b) maintaining the aqueous solution under conditions sufficient to form crystals of SSZ-65; and
(c) recovering the crystals of SSZ-65.

Accordingly, SSZ-65 may comprise the crystalline material and the SDA in combination with metallic and non-metallic oxides bonded in tetrahedral coordination through shared oxygen atoms to form a cross-linked three dimensional crystal structure. The metallic and non-metallic oxides comprise one or a combination of oxides of a first tetravalent element(s), and one or a combination of a trivalent element(s), pentavalent element(s), second tetravalent element(s) different from the first tetravalent element(s) or mixture thereof. The first tetravalent element(s) is preferably selected from the group consisting of silicon, germanium and combinations thereof. More preferably, the first tetravalent element is silicon. The trivalent element, pentavalent element and second tetravalent element (which is different from the first tetravalent element) is preferably selected from the group consisting of aluminum, gallium, iron, boron, titanium, indium, vanadium and combinations thereof. More preferably, the second trivalent or tetravalent element is aluminum or boron.

Typical sources of aluminum oxide for the reaction mixture include aluminates, alumina, aluminum colloids, aluminum oxide coated on silica sol, hydrated alumina gels such as $Al(OH)_3$ and aluminum compounds such as $AlCl_3$ and $Al_2(SO_4)_3$. Typical sources of silicon oxide include silicates, silica hydrogel, silicic acid, fumed silica, colloidal silica, tetra-alkyl orthosilicates, and silica hydroxides. Boron, as well as gallium, germanium, titanium, indium, vanadium and iron, can be added in forms corresponding to their aluminum and silicon counterparts.

A source zeolite reagent may provide a source of aluminum or boron. In most cases, the source zeolite also provides a source of silica. The source zeolite in its dealuminated or deboronated form may also be used as a source of silica, with additional silicon added using, for example, the conventional sources listed above. Use of a source zeolite reagent as a source of alumina for the present process is more completely described in U.S. Pat. No. 5,225,179, issued Jul. 6, 1993 to Nakagawa entitled "Method of Making Molecular Sieves", the disclosure of which is incorporated herein by reference.

Typically, an alkali metal hydroxide and/or an alkaline earth metal hydroxide, such as the hydroxide of sodium, potassium, lithium, cesium, rubidium, calcium, and magnesium, is used in the reaction mixture; however, this component can be omitted so long as the equivalent basicity is maintained. The SDA may be used to provide hydroxide ion. Thus, it may be beneficial to ion exchange, for example, the halide to hydroxide ion, thereby reducing or eliminating the alkali metal hydroxide quantity required. The alkali metal cation or alkaline earth cation may be part of the as-synthesized crystalline oxide material, in order to balance valence electron charges therein.

The reaction mixture is maintained at an elevated temperature until the crystals of the SSZ-65 are formed. The hydrothermal crystallization is usually conducted under autogenous pressure, at a temperature between 100° C. and 200° C., preferably between 135° C. and 160° C. The crystallization period is typically greater than 1 day and preferably from about 3 days to about 20 days.

Preferably, the molecular sieve is prepared using mild stirring or agitation.

During the hydrothermal crystallization step, the SSZ-65 crystals can be allowed to nucleate spontaneously from the reaction mixture. The use of SSZ-65 crystals as seed material can be advantageous in decreasing the time necessary for complete crystallization to occur. In addition, seeding can lead to an increased purity of the product obtained by promoting the nucleation and/or formation of SSZ-65 over any undesired phases. When used as seeds, SSZ-65 crystals are added in an amount between 0.1 and 10% of the weight of first tetravalent element oxide, e.g. silica, used in the reaction mixture.

Once the molecular sieve crystals have formed, the solid product is separated from the reaction mixture by standard mechanical separation techniques such as filtration. The crystals are water-washed and then dried, e.g., at 90° C. to 150° C. for from 8 to 24 hours, to obtain the as-synthesized SSZ-65 crystals. The drying step can be performed at atmospheric pressure or under vacuum.

SSZ-65 as prepared has a mole ratio of an oxide selected from silicon oxide, germanium oxide and mixtures thereof to an oxide selected from aluminum oxide, gallium oxide, iron oxide, boron oxide, titanium oxide, indium oxide, vanadium oxide and mixtures thereof greater than about 15; and has, after calcination, the X-ray diffraction lines of Table II below. SSZ-65 further has a composition, as synthesized (i.e., prior to removal of the SDA from the SSZ-65) and in the anhydrous state, in terms of mole ratios, shown in Table B below.

TABLE B

| As-Synthesized SSZ-65 | |
|---|---|
| $YO_2/W_cO_d$ | >15 |
| $M_{2/n}/YO_2$ | 0.01–0.03 |
| $Q/YO_2$ | 0.02–0.05 | where Y, W, M, n and Q are as defined above, c is 1 or 2, and d is 2 when c is 1 (i.e., W is tetravalent) or d is 3 or 5 when c is 2 (i.e., d is 3 when W is trivalent or 5 when W is pentavalent).

SSZ-65 can be made with a mole ratio of $YO_2W_cO_d$ of ∞, i.e., there is essentially no $W_cO_d$ present in the SSZ-65. In this case, the SSZ-65 would be an all-silica material or a germanosilicate. Thus, in a typical case where oxides of silicon and aluminum are used, SSZ-65 can be made essentially aluminum free, i.e., having a silica to alumina mole ratio of ∞. A method of increasing the mole ratio of silica to alumina is by using standard acid leaching or chelating treatments. However, essentially aluminum-free SSZ-65 can be synthesized using essentially aluminum-free silicon sources as the main tetrahedral metal oxide component, if boron is also present. The boron can then be removed, if desired, by treating the borosilicate SSZ-65 with acetic acid at elevated temperature (as described in Jones et al., Chem. Mater., 2001, 13, 1041–1050) to produce an all-silica version of SSZ-65. SSZ-65 can also be prepared directly as a borosilicate. If desired, the boron can be removed as described above and replaced with metal atoms by techniques known in the art to make, e.g., an aluminosilicate version of SSZ-65. SSZ-65 can also be prepared directly as an aluminosilicate.

Lower silica to alumina ratios may also be obtained by using methods which insert aluminum into the crystalline framework. For example, aluminum insertion may occur by thermal treatment of the zeolite in combination with an alumina binder or dissolved source of alumina. Such procedures are described in U.S. Pat. No. 4,559,315, issued on Dec. 17, 1985 to Chang et al.

It is believed that SSZ-65 is comprised of a new framework structure or topology which is characterized by its X-ray diffraction pattern. SSZ-65, as-synthesized, has a crystalline structure whose X-ray powder diffraction pattern exhibit the characteristic lines shown in Table I and is thereby distinguished from other molecular sieves.

TABLE I

As-Synthesized SSZ-65

| 2 Theta[a] | d-spacing (Angstroms) | Relative Intensity (%)[b] |
|---|---|---|
| 6.94 | 12.74 | M |
| 9.18 | 9.63 | M |
| 16.00 | 5.54 | W |
| 17.48 | 5.07 | M |
| 21.02 | 4.23 | VS |
| 21.88 | 4.06 | S |
| 22.20 | 4.00 | M |
| 23.02 | 3.86 | M |
| 26.56 | 3.36 | M |
| 28.00 | 3.19 | M |

[a]±0.1
[b]The X-ray patterns provided are based on a relative intensity scale in which the strongest line in the X-ray pattern is assigned a value of 100: W(weak) is less than 20; M(medium) is between 20 and 40; S(strong) is between 40 and 60; VS(very strong) is greater than 60.

Table IA below shows the X-ray powder diffraction lines for as-synthesized SSZ-65 including actual relative intensities.

TABLE IA

| 2 Theta[a] | d-spacing (Angstroms) | Relative Intensity (%) |
|---|---|---|
| 6.94 | 12.74 | 26.7 |
| 9.18 | 9.63 | 22.7 |
| 16.00 | 5.54 | 14.2 |
| 17.48 | 5.07 | 25.8 |

TABLE IA-continued

| 2 Theta[a] | d-spacing (Angstroms) | Relative Intensity (%) |
|---|---|---|
| 21.02 | 4.23 | 100.0 |
| 21.88 | 4.06 | 47.8 |
| 22.20 | 4.00 | 27.0 |
| 23.02 | 3.86 | 36.8 |
| 26.56 | 3.36 | 21.9 |
| 28.00 | 3.19 | 27.0 |

[a]±0.1

After calcination, the SSZ-65 molecular sieves have a crystalline structure whose X-ray powder diffraction pattern include the characteristic lines shown in Table II:

TABLE II

Calcined SSZ-65

| 2 Theta[a] | d-spacing (Angstroms) | Relative Intensity (%) |
|---|---|---|
| 6.08 | 14.54 | M |
| 6.98 | 12.66 | VS |
| 9.28 | 9.53 | S |
| 17.58 | 5.04 | M |
| 21.14 | 4.20 | VS |
| 21.98 | 4.04 | S |
| 22.26 | 3.99 | M |
| 23.14 | 3.84 | M |
| 26.68 | 3.34 | M |
| 28.10 | 3.18 | M |

[a]±0.1

Table IIA below shows the X-ray powder diffraction lines for calcined SSZ-65 including actual relative intensities.

TABLE IIA

| 2 Theta[a] | d-spacing (Angstroms) | Relative Intensity (%) |
|---|---|---|
| 6.08 | 14.54 | 37.7 |
| 6.98 | 12.66 | 82.8 |
| 9.28 | 9.53 | 50.7 |
| 17.58 | 5.04 | 28.2 |
| 21.14 | 4.20 | 100.0 |
| 21.98 | 4.04 | 47.8 |
| 22.26 | 3.99 | 19.6 |
| 23.14 | 3.84 | 28.3 |
| 26.68 | 3.34 | 20.4 |
| 28.10 | 3.18 | 26.8 |

[a]±0.1

The X-ray powder diffraction patterns were determined by standard techniques. The radiation was the K-alpha/doublet of copper. The peak heights and the positions, as a function of 2θ where θ is the Bragg angle, were read from the relative intensities of the peaks, and d, the interplanar spacing in Angstroms corresponding to the recorded lines, can be calculated.

The variation in the scattering angle (two theta) measurements, due to instrument error and to differences between individual samples, is estimated at ±0.1 degrees.

The X-ray diffraction pattern of Table I is representative of "as-synthesized" or "as-made" SSZ-65 molecular sieves. Minor variations in the diffraction pattern can result from variations in the silica-to-alumina or silica-to-boron mole ratio of the particular sample due to changes in lattice constants. In addition, sufficiently small crystals will affect the shape and intensity of peaks, leading to significant peak broadening.

Representative peaks from the X-ray diffraction pattern of calcined SSZ-65 are shown in Table II. Calcination can also result in changes in the intensities of the peaks as compared to patterns of the "as-made" material, as well as minor shifts in the diffraction pattern. The molecular sieve produced by exchanging the metal or other cations present in the molecular sieve with various other cations (such as $H^+$ or $NH_4^+$) yields essentially the same diffraction pattern, although again, there may be minor shifts in the interplanar spacing and variations in the relative intensities of the peaks. Notwithstanding these minor perturbations, the basic crystal lattice remains unchanged by these treatments.

Crystalline SSZ-65 can be used as-synthesized, but preferably will be thermally treated (calcined). Usually, it is desirable to remove the alkali metal cation by ion exchange and replace it with hydrogen, ammonium, or any desired metal ion. The molecular sieve can be leached with chelating agents, e.g., EDTA or dilute acid solutions, to increase the silica to alumina mole ratio. The molecular sieve can also be steamed; steaming helps stabilize the crystalline lattice to attack from acids.

The molecular sieve can be used in intimate combination with hydrogenating components, such as tungsten, vanadium, molybdenum, rhenium, nickel, cobalt, chromium, manganese, or a noble metal, such as palladium or platinum, for those applications in which a hydrogenation-dehydrogenation function is desired.

Metals may also be introduced into the molecular sieve by replacing some of the cations in the molecular sieve with metal cations via standard ion exchange techniques (see, for example, U.S. Pat. No. 3,140,249 issued Jul. 7, 1964 to Plank et al.; U.S. Pat. No. 3,140,251 issued Jul. 7, 1964 to Plank et al.; and U.S. Pat. No. 3,140,253 issued Jul. 7, 1964 to Plank et al.). Typical replacing cations can include metal cations, e.g., rare earth, Group IA, Group IIA and Group VIII metals, as well as their mixtures. Of the replacing metallic cations, cations of metals such as rare earth, Mn, Ca, Mg, Zn, Cd, Pt, Pd, Ni, Co, Ti, Al, Sn, and Fe are particularly preferred.

The hydrogen, ammonium, and metal components can be ion-exchanged into the SSZ-65. The SSZ-65 can also be impregnated with the metals, or the metals can be physically and intimately admixed with the SSZ-65 using standard methods known to the art.

Typical ion-exchange techniques involve contacting the synthetic molecular sieve with a solution containing a salt of the desired replacing cation or cations. Although a wide variety of salts can be employed, chlorides and other halides, acetates, nitrates, and sulfates are particularly preferred. The molecular sieve is usually calcined prior to the ion-exchange procedure to remove the organic matter present in the channels and on the surface, since this results in a more effective ion exchange. Representative ion exchange techniques are disclosed in a wide variety of patents including U.S. Pat. Nos. 3,140,249 issued on Jul. 7, 1964 to Plank et al.; U.S. Pat. No. 3,140,251 issued on Jul. 7, 1964 to Plank et al.; and U.S. Pat. No. 3,140,253 issued on Jul. 7, 1964 to Plank et al.

Following contact with the salt solution of the desired replacing cation, the molecular sieve is typically washed with water and dried at temperatures ranging from 65° C. to about 200° C. After washing, the molecular sieve can be calcined in air or inert gas at temperatures ranging from about 200° C. to about 800° C. for periods of time ranging from 1 to 48 hours, or more, to produce a catalytically active product especially useful in hydrocarbon conversion processes.

Regardless of the cations present in the synthesized form of SSZ-65, the spatial arrangement of the atoms which form the basic crystal lattice of the molecular sieve remains essentially unchanged.

SSZ-65 can be formed into a wide variety of physical shapes. Generally speaking, the molecular sieve can be in the form of a powder, a granule, or a molded product, such as extrudate having a particle size sufficient to pass through a 2-mesh (Tyler) screen and be retained on a 400-mesh (Tyler) screen. In cases where the catalyst is molded, such as by extrusion with an organic binder, the SSZ-65 can be extruded before drying, or, dried or partially dried and then extruded.

SSZ-65 can be composited with other materials resistant to the temperatures and other conditions employed in organic conversion processes. Such matrix materials include active and inactive materials and synthetic or naturally occurring zeolites as well as inorganic materials such as clays, silica and metal oxides. Examples of such materials and the manner in which they can be used are disclosed in U.S. Pat. No. 4,910,006, issued May 20, 1990 to Zones et al., and U.S. Pat. No. 5,316,753, issued May 31, 1994 to Nakagawa, both of which are incorporated by reference herein in their entirety.

Hydrocarbon Conversion Processes

SSZ-65 zeolites are useful in hydrocarbon conversion reactions. Hydrocarbon conversion reactions are chemical and catalytic processes in which carbon containing compounds are changed to different carbon containing compounds. Examples of hydrocarbon conversion reactions in which SSZ-65 are expected to be useful include hydrocracking, dewaxing, catalytic cracking and olefin and aromatics formation reactions. The catalysts are also expected to be useful in other petroleum refining and hydrocarbon conversion reactions such as isomerizing n-paraffins and naphthenes, polymerizing and oligomerizing olefinic or acetylenic compounds such as isobutylene and butene-1, reforming, isomerizing polyalkyl substituted aromatics (e.g., m-xylene), and disproportionating aromatics (e.g., toluene) to provide mixtures of benzene, xylenes and higher methylbenzenes and oxidation reactions. Also included are rearrangement reactions to make various naphthalene derivatives, and forming higher molecular weight hydrocarbons from lower molecular weight hydrocarbons (e.g., methane upgrading). The SSZ-65 catalysts may have high selectivity, and under hydrocarbon conversion conditions can provide a high percentage of desired products relative to total products.

For high catalytic activity, the SSZ-65 zeolite should be predominantly in its hydrogen ion form. Generally, the zeolite is converted to its hydrogen form by ammonium exchange followed by calcination. If the zeolite is synthesized with a high enough ratio of SDA cation to sodium ion, calcination alone may be sufficient. It is preferred that, after calcination, at least 80% of the cation sites are occupied by hydrogen ions and/or rare earth ions. As used herein, "predominantly in the hydrogen form" means that, after calcination, at least 80% of the cation sites are occupied by hydrogen ions and/or rare earth ions.

SSZ-65 zeolites can be used in processing hydrocarbonaceous feedstocks. Hydrocarbonaceous feedstocks contain carbon compounds and can be from many different sources, such as virgin petroleum fractions, recycle petroleum fractions, shale oil, liquefied coal, tar sand oil, synthetic paraffins from NAO, recycled plastic feedstocks and, in general, can be any carbon containing feedstock susceptible to zeolitic catalytic reactions. Depending on the type of processing the hydrocarbonaceous feed is to undergo, the feed can contain metal or be free of metals, it can also have high or low nitrogen or sulfur impurities. It can be appreciated, however, that in general processing will be more efficient (and the catalyst more active) the lower the metal, nitrogen, and sulfur content of the feedstock.

The conversion of hydrocarbonaceous feeds can take place in any convenient mode, for example, in fluidized bed, moving bed, or fixed bed reactors depending on the types of process desired. The formulation of the catalyst particles will vary depending on the conversion process and method of operation.

Other reactions which can be performed using the catalyst of this invention containing a metal, e.g., a Group VIII metal such platinum, include hydrogenation-dehydrogenation reactions, denitrogenation and desulfurization reactions.

The following table indicates typical reaction conditions which may be employed when using catalysts comprising SSZ-65 in the hydrocarbon conversion reactions of this invention. Preferred conditions are indicated in parentheses.

| Process | Temp., °C. | Pressure | LHSV |
|---|---|---|---|
| Hydrocracking | 175–485 | 0.5–350 bar | 0.1–30 |
| Dewaxing | 200–475 (250–450) | 15–3000 psig, 0.103–20.7 MPa gauge (200–3000, 1.38–20.7 MPa gauge) | 0.1–20 (0.2–10) |
| Aromatics formation | 400–600 (480–550) | atm.–10 bar | 0.1–15 |
| Cat. cracking | 127–885 | subatm.-$^1$ (atm.–5 atm.) | 0.5–50 |
| Oligomerization | 232–649$^2$ 10–232$^4$ (27–204)$^4$ | 0.1–50 atm.$^{2,3}$ — — | 0.2–50$^2$ 0.05–20$^5$ (0.1–10)$^5$ |
| Paraffins to aromatics | 100–700 | 0–1000 psig | 0.5–40$^5$ |
| Condensation of alcohols | 260–538 | 0.5–1000 psig, 0.00345–6.89 MPa gauge | 0.5–50$^5$ |
| Isomerization | 93–538 (204–315) | 50–1000 psig, 0.345–6.89 MPa gauge | 1–10 (1–4) |
| Xylene isomerization | 260–593$^2$ (315–566)$^2$ 38–371$^4$ | 0.5–50 atm.$^2$ (1–5 atm)$^2$ 1–200 atm.$^4$ | 0.1–100$^5$ (0.5–50)$^5$ 0.5–50 |

$^1$Several hundred atmospheres
$^2$Gas phase reaction
$^3$Hydrocarbon partial pressure
$^4$Liquid phase reaction
$^5$WHSV Other reaction conditions and parameters are provided below.

Hydrocracking

Using a catalyst which comprises SSZ-65, preferably predominantly in the hydrogen form, and a hydrogenation promoter, heavy petroleum residual feedstocks, cyclic stocks and other hydrocrackate charge stocks can be hydrocracked using the process conditions and catalyst components disclosed in the aforementioned U.S. Pat. No. 4,910,006 and U.S. Pat. No. 5,316,753.

The hydrocracking catalysts contain an effective amount of at least one hydrogenation component of the type commonly employed in hydrocracking catalysts. The hydrogenation component is generally selected from the group of hydrogenation catalysts consisting of one or more metals of Group VIB and Group VIII, including the salts, complexes and solutions containing such. The hydrogenation catalyst is preferably selected from the group of metals, salts and complexes thereof of the group consisting of at least one of platinum, palladium, rhodium, iridium, ruthenium and mixtures thereof or the group consisting of at least one of nickel, molybdenum, cobalt, tungsten, titanium, chromium and mixtures thereof. Reference to the catalytically active metal or metals is intended to encompass such metal or metals in the elemental state or in some form such as an oxide, sulfide, halide, carboxylate and the like. The hydrogenation catalyst is present in an effective amount to provide the hydrogenation function of the hydrocracking catalyst, and preferably in the range of from 0.05 to 25% by weight.

Dewaxing

SSZ-65, preferably predominantly in the hydrogen form, can be used to dewax hydrocarbonaceous feeds by selectively removing straight chain paraffins. Typically, the viscosity index of the dewaxed product is improved (compared to the waxy feed) when the waxy feed is contacted with SSZ-65 under isomerization dewaxing conditions.

The catalytic dewaxing conditions are dependent in large measure on the feed used and upon the desired pour point. Hydrogen is preferably present in the reaction zone during the catalytic dewaxing process. The hydrogen to feed ratio is typically between about 500 and about 30,000 SCF/bbl (standard cubic feet per barrel) (0.089 to 5.34 SCM/liter (standard cubic meters/liter)), preferably about 1000 to about 20,000 SCF/bbl (0.178 to 3.56 SCM/liter). Generally, hydrogen will be separated from the product and recycled to the reaction zone. Typical feedstocks include light gas oil, heavy gas oils and reduced crudes boiling above about 350° F. (177° C.).

A typical dewaxing process is the catalytic dewaxing of a hydrocarbon oil feedstock boiling above about 350° F. (177° C.) and containing straight chain and slightly branched chain hydrocarbons by contacting the hydrocarbon oil feedstock in the presence of added hydrogen gas at a hydrogen pressure of about 15–3000 psi (0.103–20.7 MPa) with a catalyst comprising SSZ-65 and at least one Group VIII metal.

The SSZ-65 hydrodewaxing catalyst may optionally contain a hydrogenation component of the type commonly employed in dewaxing catalysts. See the aforementioned U.S. Pat. No. 4,910,006 and U.S. Pat. No. 5,316,753 for examples of these hydrogenation components.

The hydrogenation component is present in an effective amount to provide an effective hydrodewaxing and hydroisomerization catalyst preferably in the range of from about 0.05 to 5% by weight. The catalyst may be run in such a mode to increase isomerization dewaxing at the expense of cracking reactions.

The feed may be hydrocracked, followed by dewaxing. This type of two stage process and typical hydrocracking conditions are described in U.S. Pat. No. 4,921,594, issued May 1, 1990 to Miller, which is incorporated herein by reference in its entirety.

SSZ-65 may also be utilized as a dewaxing catalyst in the form of a layered catalyst. That is, the catalyst comprises a first layer comprising zeolite SSZ-65 and at least one Group VIII metal, and a second layer comprising an aluminosilicate zeolite which is more shape selective than zeolite SSZ-65. The use of layered catalysts is disclosed in U.S. Pat. No. 5,149,421, issued Sep. 22, 1992 to Miller, which is incorporated by reference herein in its entirety. The layering may also include a bed of SSZ-65 layered with a non-zeolitic component designed for either hydrocracking or hydrofinishing.

SSZ-65 may also be used to dewax raffinates, including bright stock, under conditions such as those disclosed in U.S. Pat. No. 4,181,598, issued Jan. 1, 1980 to Gillespie et al., which is incorporated by reference herein in its entirety.

It is often desirable to use mild hydrogenation (sometimes referred to as hydrofinishing) to produce more stable dewaxed products. The hydrofinishing step can be performed either before or after the dewaxing step, and preferably after. Hydrofinishing is typically conducted at temperatures ranging from about 190° C. to about 340° C. at pressures from about 400 psig to about 3000 psig (2.76 to 20.7 MPa gauge) at space velocities (LHSV) between about 0.1 and 20 and a hydrogen recycle rate of about 400 to 1500 SCF/bbl (0.071 to 0.27 SCM/liter). The hydrogenation catalyst employed must be active enough not only to hydrogenate the olefins, diolefins and color bodies which may be present, but also to reduce the aromatic content. Suitable hydrogenation catalyst are disclosed in U.S. Pat. No. 4,921,594, issued May 1, 1990 to Miller, which is incorporated by reference herein in its entirety. The hydrofinishing step is beneficial in preparing an acceptably stable product (e.g., a lubricating oil) since dewaxed products prepared from hydrocracked stocks tend to be unstable to air and light and tend to form sludges spontaneously and quickly.

Lube oil may be prepared using SSZ-65. For example, a $C_{20+}$ lube oil may be made by isomerizing a $C_{20+}$ olefin feed over a catalyst comprising SSZ-65 in the hydrogen form and at least one Group VIII metal. Alternatively, the lubricating oil may be made by hydrocracking in a hydrocracking zone a hydrocarbonaceous feedstock to obtain an effluent comprising a hydrocracked oil, and catalytically dewaxing the effluent at a temperature of at least about 400° F. (204° C.) and at a pressure of from about 15 psig to about 3000 psig (0.103–20.7 MPa gauge) in the presence of added hydrogen gas with a catalyst comprising SSZ-65 in the hydrogen form and at least one Group VIII metal.

Aromatics Formation

SSZ-65 can be used to convert light straight run naphthas and similar mixtures to highly aromatic mixtures. Thus, normal and slightly branched chained hydrocarbons, preferably having a boiling range above about 40° C. and less than about 200° C., can be converted to products having a substantial higher octane aromatics content by contacting the hydrocarbon feed with a catalyst comprising SSZ-65. It is also possible to convert heavier feeds into BTX or naphthalene derivatives of value using a catalyst comprising SSZ-65.

The conversion catalyst preferably contains a Group VIII metal compound to have sufficient activity for commercial use. By Group vm metal compound as used herein is meant the metal itself or a compound thereof. The Group VIII noble metals and their compounds, platinum, palladium, and iridium, or combinations thereof can be used. Rhenium or tin or a mixture thereof may also be used in conjunction with the Group VIII metal compound and preferably a noble metal compound. The most preferred metal is platinum. The amount of Group VIII metal present in the conversion catalyst should be within the normal range of use in reforming catalysts, from about 0.05 to 2.0 weight percent, preferably 0.2 to 0.8 weight percent.

It is critical to the selective production of aromatics in useful quantities that the conversion catalyst be substantially free of acidity, for example, by neutralizing the zeolite with a basic metal, e.g., alkali metal, compound. Methods for rendering the catalyst free of acidity are known in the art. See the aforementioned U.S. Pat. No. 4,910,006 and U.S. Pat. No. 5,316,753 for a description of such methods.

The preferred alkali metals are sodium, potassium, rubidium and cesium. The zeolite itself can be substantially free of acidity only at very high silica:alumina mole ratios.

Catalytic Cracking

Hydrocarbon cracking stocks can be catalytically cracked in the absence of hydrogen using SSZ-65, preferably predominantly in the hydrogen form.

When SSZ-65 is used as a catalytic cracking catalyst in the absence of hydrogen, the catalyst may be employed in conjunction with traditional cracking catalysts, e.g., any aluminosilicate heretofore employed as a component in cracking catalysts. Typically, these are large pore, crystalline aluminosilicates. Examples of these traditional cracking catalysts are disclosed in the aforementioned U.S. Pat. No. 4,910,006 and U.S. Pat. No 5,316,753. When a traditional cracking catalyst (TC) component is employed, the relative weight ratio of the TC to the SSZ-65 is generally between about 1:10 and about 500:1, desirably between about 1:10 and about 200:1, preferably between about 1:2 and about 50:1, and most preferably is between about 1:1 and about 20:1. The novel zeolite and/or the traditional cracking component may be further ion exchanged with rare earth ions to modify selectivity.

The cracking catalysts are typically employed with an inorganic oxide matrix component. See the aforementioned U.S. Pat. No. 4,910,006 and U.S. Pat. No. 5,316,753 for examples of such matrix components.

Isomerization

The present catalyst is highly active and highly selective for isomerizing $C_4$ to $C_7$ hydrocarbons. The activity means that the catalyst can operate at relatively low temperature which thermodynamically favors highly branched paraffins. Consequently, the catalyst can produce a high octane product. The high selectivity means that a relatively high liquid yield can be achieved when the catalyst is run at a high octane.

The present process comprises contacting the isomerization catalyst, i.e., a catalyst comprising SSZ-65 in the hydrogen form, with a hydrocarbon feed under isomerization conditions. The feed is preferably a light straight run fraction, boiling within the range of 30° F. to 250° F. (−1° C. to 121° C.) and preferably from 60° F. to 200° F. (16° C. to 93° C.). Preferably, the hydrocarbon feed for the process comprises a substantial amount of $C_4$ to $C_7$ normal and slightly branched low octane hydrocarbons, more preferably $C_5$ and $C_6$ hydrocarbons.

It is preferable to carry out the isomerization reaction in the presence of hydrogen. Preferably, hydrogen is added to give a hydrogen to hydrocarbon ratio ($H_2$/HC) of between 0.5 and 10 $H_2$/HC, more preferably between 1 and 8 $H_2$/HC. See the aforementioned U.S. Pat. No. 4,910,006 and U.S. Pat. No. 5,316,753 for a further discussion of isomerization process conditions.

A low sulfur feed is especially preferred in the present process. The feed preferably contains less than 10 ppm, more preferably less than 1 ppm, and most preferably less than 0.1 ppm sulfur. In the case of a feed which is not already low in sulfur, acceptable levels can be reached by hydrogenating the feed in a presaturation zone with a hydrogenating catalyst which is resistant to sulfur poisoning. See the aforementioned U.S. Pat. No. 4,910,006 and U.S. Pat. No. 5,316,753 for a further discussion of this hydrodesulfurization process.

It is preferable to limit the nitrogen level and the water content of the feed. Catalysts and processes which are suitable for these purposes are known to those skilled in the art.

After a period of operation, the catalyst can become deactivated by sulfur or coke. See the aforementioned U.S. Pat. No. 4,910,006 and U.S. Pat. No. 5,316,753 for a further discussion of methods of removing this sulfur and coke, and of regenerating the catalyst.

The conversion catalyst preferably contains a Group VIII metal compound to have sufficient activity for commercial use. By Group VIII metal compound as used herein is meant the metal itself or a compound thereof. The Group VIII noble metals and their compounds, platinum, palladium, and iridium, or combinations thereof can be used. Rhenium and tin may also be used in conjunction with the noble metal. The most preferred metal is platinum. The amount of Group VIII metal present in the conversion catalyst should be within the normal range of use in isomerizing catalysts, from about 0.05 to 2.0 weight percent, preferably 0.2 to 0.8 weight percent.

Alkylation and Transalkylation

SSZ-65 can be used in a process for the alkylation or transalkylation of an aromatic hydrocarbon. The process comprises contacting the aromatic hydrocarbon with a $C_2$ to $C_{16}$ olefin alkylating agent or a polyalkyl aromatic hydrocarbon transalkylating agent, under at least partial liquid phase conditions, and in the presence of a catalyst comprising SSZ-65.

SSZ-65 can also be used for removing benzene from gasoline by alkylating the benzene as described above and removing the alkylated product from the gasoline.

For high catalytic activity, the SSZ-65 zeolite should be predominantly in its hydrogen ion form. It is preferred that, after calcination, at least 80% of the cation sites are occupied by hydrogen ions and/or rare earth ions.

Examples of suitable aromatic hydrocarbon feedstocks which may be alkylated or transalkylated by the process of the invention include aromatic compounds such as benzene, toluene and xylene. The preferred aromatic hydrocarbon is benzene. There may be occasions where naphthalene or naphthalene derivatives such as dimethylnaphthalene may be desirable. Mixtures of aromatic hydrocarbons may also be employed.

Suitable olefins for the alkylation of the aromatic hydrocarbon are those containing 2 to 20, preferably 2 to 4, carbon atoms, such as ethylene, propylene, butene-1, trans-butene-2 and cis-butene-2, or mixtures thereof. There may be instances where pentenes are desirable. The preferred olefins are ethylene and propylene. Longer chain alpha olefins may be used as well.

When transalkylation is desired, the transalkylating agent is a polyalkyl aromatic hydrocarbon containing two or more alkyl groups that each may have from 2 to about 4 carbon atoms. For example, suitable polyalkyl aromatic hydrocarbons include di-, tri- and tetra-alkyl aromatic hydrocarbons, such as diethylbenzene, triethylbenzene, diethylmethylbenzene (diethyltoluene), di-isopropylbenzene, di-isopropyltoluene, dibutylbenzene, and the like. Preferred polyalkyl aromatic hydrocarbons are the dialkyl benzenes. A particularly preferred polyalkyl aromatic hydrocarbon is di-isopropylbenzene.

When alkylation is the process conducted, reaction conditions are as follows. The aromatic hydrocarbon feed should be present in stoichiometric excess. It is preferred that molar ratio of aromatics to olefins be greater than four-to-one to prevent rapid catalyst fouling. The reaction temperature may range from 1 00° F. to 600° F. (38° C. to 315° C.), preferably 250° F. to 450° F. (121° C. to 232° C.). The reaction pressure should be sufficient to maintain at least a partial liquid phase in order to retard catalyst fouling. This is typically 50 psig to 1000 psig (0.345 to 6.89 MPa gauge) depending on the feedstock and reaction temperature. Contact time may range from 10 seconds to 10 hours, but is usually from 5 minutes to an hour. The weight hourly space velocity (WHSV), in terms of grams (pounds) of aromatic hydrocarbon and olefin per gram (pound) of catalyst per hour, is generally within the range of about 0.5 to 50.

When transalkylation is the process conducted, the molar ratio of aromatic hydrocarbon will generally range from about 1:1 to 25:1, and preferably from about 2:1 to 20:1. The reaction temperature may range from about 100° F. to 600° F. (38° C. to 315° C.), but it is preferably about 250° F. to 450° F. (121° C. to 232° C.). The reaction pressure should be sufficient to maintain at least a partial liquid phase, typically in the range of about 50 psig to 1000 psig (0.345 to 6.89 MPa gauge), preferably 300 psig to 600 psig (2.07 to 4.14 MPa gauge). The weight hourly space velocity will range from about 0.1 to 10. U.S. Pat. No. 5,082,990 issued on Jan. 21, 1992 to Hsieh, et al. describes such processes and is incorporated herein by reference.

Conversion of Paraffins to Aromatics

SSZ-65 can be used to convert light gas $C_2$–$C_6$ paraffins to higher molecular weight hydrocarbons including aromatic compounds. Preferably, the zeolite will contain a catalyst metal or metal oxide wherein said metal is selected from the group consisting of Groups IB, IIB, VIII and IIIA of the Periodic Table. Preferably, the metal is gallium, niobium, indium or zinc in the range of from about 0.05 to 5% by weight.

Isomerization of Olefins

SSZ-65 can be used to isomerize olefins. The feed stream is a hydrocarbon stream containing at least one $C_{4-6}$ olefin, preferably a $C_{4-6}$ normal olefin, more preferably normal butene. Normal butene as used in this specification means all forms of normal butene, e.g., 1-butene, cis-2-butene, and trans-2-butene. Typically, hydrocarbons other than normal butene or other $C_{4-6}$ normal olefins will be present in the feed stream. These other hydrocarbons may include, e.g., alkanes, other olefins, aromatics, hydrogen, and inert gases.

The feed stream typically may be the effluent from a fluid catalytic cracking unit or a methyl-tert-butyl ether unit. A fluid catalytic cracking unit effluent typically contains about 40–60 weight percent normal butenes. A methyl-tert-butyl ether unit effluent typically contains 40–100 weight percent normal butene. The feed stream preferably contains at least about 40 weight percent normal butene, more preferably at least about 65 weight percent normal butene. The terms iso-olefin and methyl branched iso-olefin may be used interchangeably in this specification.

The process is carried out under isomerization conditions. The hydrocarbon feed is contacted in a vapor phase with a catalyst comprising the SSZ-65. The process may be carried out generally at a temperature from about 625° F. to about 950° F. (329–510° C.), for butenes, preferably from about 700° F. to about 900° F. (371–482° C.), and about 350° F. to about 650° F. (177–343° C.) for pentenes and hexenes. The pressure ranges from subatmospheric to about 200 psig (1.38 MPa gauge), preferably from about 15 psig to about 200 psig (0.103 to 1.38 MPa gauge), and more preferably from about 1 psig to about 150 psig (0.00689 to 1.03 MPa gauge).

The liquid hourly space velocity during contacting is generally from about 0.1 to about 50 $hr^{-1}$, based on the hydrocarbon feed, preferably from about 0.1 to about 20 $hr^{-1}$, more preferably from about 0.2 to about 10 $hr^{-1}$, most preferably from about 1 to about 5 $hr^{-1}$. A hydrogen/hydrocarbon molar ratio is maintained from about 0 to about 30 or higher. The hydrogen can be added directly to the feed stream or directly to the isomerization zone. The reaction is preferably substantially free of water, typically less than about two weight percent based on the feed. The process can be carried out in a packed bed reactor, a fixed bed, fluidized bed reactor, or a moving bed reactor. The bed of the catalyst can move upward or downward. The mole percent conversion of, e.g., normal butene to iso-butene is at least 10, preferably at least 25, and more preferably at least 35.

Xylene Isomerization

SSZ-65 may also be useful in a process for isomerizing one or more xylene isomers in a $C_8$ aromatic feed to obtain ortho-, meta-, and para-xylene in a ratio approaching the equilibrium value. In particular, xylene isomerization is used in conjunction with a separate process to manufacture para-xylene. For example, a portion of the para-xylene in a mixed $C_8$ aromatics stream may be recovered by crystallization and centrifugation. The mother liquor from the crystallizer is then reacted under xylene isomerization conditions to restore ortho-, meta- and para-xylenes to a near equilibrium ratio. At the same time, part of the ethylbenzene in the mother liquor is converted to xylenes or to products which are easily separated by filtration. The isomerate is blended with fresh feed and the combined stream is distilled to remove heavy and light by-products. The resultant $C_8$ aromatics stream is then sent to the crystallizer to repeat the cycle.

Optionally, isomerization in the vapor phase is conducted in the presence of 3.0 to 30.0 moles of hydrogen per mole of alkylbenzene (e.g., ethylbenzene). If hydrogen is used, the catalyst should comprise about 0.1 to 2.0 wt. % of a hydrogenation/dehydrogenation component selected from Group VIII (of the Periodic Table) metal component, especially platinum or nickel. By Group VIII metal component is meant the metals and their compounds such as oxides and sulfides.

Optionally, the isomerization feed may contain 10 to 90 wt. of a diluent such as toluene, trimethylbenzene, naphthenes or paraffins.

Oligomerization

It is expected that SSZ-65 can also be used to oligomerize straight and branched chain olefins having from about 2 to 21 and preferably 2–5 carbon atoms. The oligomers which are the products of the process are medium to heavy olefins which are useful for both fuels, i.e., gasoline or a gasoline blending stock and chemicals.

The oligomerization process comprises contacting the olefin feedstock in the gaseous or liquid phase with a catalyst comprising SSZ-65.

The zeolite can have the original cations associated therewith replaced by a wide variety of other cations according to techniques well known in the art. Typical cations would include hydrogen, ammonium and metal cations including mixtures of the same. Of the replacing metallic cations, particular preference is given to cations of metals such as rare earth metals, manganese, calcium, as well as metals of Group II of the Periodic Table, e.g., zinc, and Group VIII of the Periodic Table, e.g., nickel. One of the prime requisites is that the zeolite have a fairly low aromatization activity, i.e., in which the amount of aromatics produced is not more than about 20% by weight. This is accomplished by using a zeolite with controlled acid activity [alpha value] of from about 0.1 to about 120, preferably from about 0.1 to about 100, as measured by its ability to crack n-hexane.

Alpha values are defined by a standard test known in the art, e.g., as shown in U.S. Pat. No. 3,960,978 issued on Jun. 1, 1976 to Givens et al. which is incorporated totally herein by reference. If required, such zeolites may be obtained by steaming, by use in a conversion process or by any other method which may occur to one skilled in this art.

Condensation of Alcohols

SSZ-65 can be used to condense lower aliphatic alcohols having 1 to 10 carbon atoms to a gasoline boiling point hydrocarbon product comprising mixed aliphatic and aromatic hydrocarbon. The process disclosed in U.S. Pat. No. 3,894,107, issued Jul. 8, 1975 to Butter et al., describes the process conditions used in this process, which patent is incorporated totally herein by reference.

The catalyst may be in the hydrogen form or may be base exchanged or impregnated to contain ammonium or a metal cation complement, preferably in the range of from about 0.05 to 5% by weight. The metal cations that may be present include any of the metals of the Groups I through VIII of the Periodic Table. However, in the case of Group IA metals, the cation content should in no case be so large as to effectively inactivate the catalyst, nor should the exchange be such as to eliminate all acidity. There may be other processes involving treatment of oxygenated substrates where a basic catalyst is desired.

Methane Upgrading

Higher molecular weight hydrocarbons can be formed from lower molecular weight hydrocarbons by contacting the lower molecular weight hydrocarbon with a catalyst comprising SSZ-65 and a metal or metal compound capable of converting the lower molecular weight hydrocarbon to a higher molecular weight hydrocarbon. Examples of such reactions include the conversion of methane to $C_{2+}$ hydrocarbons such as ethylene or benzene or both. Examples of useful metals and metal compounds include lanthanide and or actinide metals or metal compounds.

These reactions, the metals or metal compounds employed and the conditions under which they can be run are disclosed in U.S. Patents No. 4,734,537, issued Mar. 29, 1988 to Devries et al.; U.S. Pat. No. 4,939,311, issued Jul. 3, 1990 to Washechecket al.; U.S. Pat. No. 4,962,261, issued Oct. 9, 1990 to Abrevaya et al.; U.S. Pat. No. 5,095,161, issued Mar. 10, 1992 to Abrevaya et al.; U.S. Pat. No. 5,105,044, issued Apr. 14, 1992 to Han et al.; U.S. Pat. No. 5,105,046, issued Apr. 14, 1992 to Washecheck; U.S. Pat. No. 5,238,898, issued Aug. 24, 1993 to Han et al.; U.S. Pat. No. 5,321,185, issued Jun. 14, 1994 to van der Vaart; and U.S. Pat. No. 5,336,825, issued Aug. 9, 1994 to Choudhary et al., each of which is incorporated herein by reference in its entirety.

EXAMPLES

The following examples demonstrate but do not limit the present invention.

Example 1

Synthesis of SDA 1-[1-(4-chlorophenyl)-cyclopropylmethyl]-1-ethyl-pyrrolidinium Cation

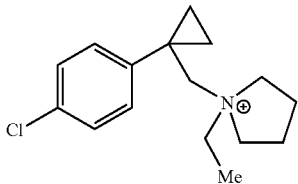

1-[1-(4-Chloro-phenyl)-cyclopropylmethyl]-1-ethyl-pyrrolidinium

The structure directing agent is synthesized according to the synthetic scheme shown below (Scheme 1).

1-[1-(4-chloro-phenyl)-cyclopropylmethyl]-1-ethyl-pyrrolidinium iodide is prepared from the reaction of the parent amine 1-[1-(4-chloro-phenyl)-cyclopropylmethyl]-pyrrolidine with ethyl iodide. A 100 gm (0.42 mole) of the amine, 1-[1-(4-chloro-phenyl)-cyclopropylmethyl]-pyrrolidine, is dissolved in 1000 ml anhydrous methanol in a 3-litre 3-necked reaction flask (equipped with a mechanical stirrer and a reflux condenser). To this solution, 98 gm (0.62 mole) of ethyl iodide is added, and the mixture is stirred at room temperature for 72 hours. Then, 39 gm (0.25 mol.) of ethyl iodide is added and the mixture is heated at reflux for 3 hours. The reaction mixture is cooled down and excess ethyl iodide and the solvent are removed at reduced pressure on a rotary evaporator. The obtained dark tan-colored solids (162 gm) are further purified by dissolving in acetone (500 ml) followed by precipitation by adding diethyl ether. Filtration and air-drying the obtained solids gives 153 gm (93% yield) of the desired 1-[1-(4-chloro-phenyl)-cyclopropylmethyl]-1-ethyl-pyrrolidinium iodide as a white powder. The product is pure by $^1$H and $^{13}$C-NMR analysis.

The hydroxide form of 1-[1-(4-chloro-phenyl)-cyclopropyhnethyl]-1-ethyl-pyrrolidinium cation is obtained by an ion exchange treatment of the iodide salt with Ion-Exchange Resin-OH (BIO RAD® AH1-X8). In a 1-liter volume plastic bottle, 100 gm (255 mmol) of 1-[1-(4-chloro-phenyl)-cyclopropylmethyl]-1-ethyl-pyrrolidinium iodide is dissolved in 300 ml de-ionized water. Then, 320 gm of the ion exchange resin is added and the solution is allowed to gently stir overnight. The mixture is then filtered, and the resin cake is rinsed with minimal amount of de-ionized water. The filtrate is analyzed for hydroxide concentration by titration analysis on a small sample of the solution with 0.1N HCl. The reaction yields 96% of (245 mmol) of the desired 1-[1-(4-chloro-phenyl)-cyclopropylmethyl]-1-ethyl-pyrrolidinium hydroxide (hydroxide concentration of 0.6 M).

The parent amine 1-[1-(4-chloro-phenyl)-cyclopropylmethyl]-pyrrolidine is obtained from the LiAlH$_4$-reduction of the precursor amide [1-(4-chloro-phenyl)-cyclopropyl]-pyrrolidin-1-yl-methanone. In a 3-neck 3-liter reaction flask equipped with a mechanical stirrer and reflux condenser, 45.5 gm (1.2 mol.) of LiAlH$_4$ is suspended in 750 ml anhydrous tetrahydrofuran (THF). The suspension is cooled down to 0° C. (ice-bath), and 120 gm (0.48 mole) of [1-(4-chloro-phenyl)-cyclopropyl]-pyrrolidin-1-yl-methanone dissolved in 250 ml THF is added (to the suspension) drop-wise via an addition funnel. Once all the amide solution is added, the ice-bath is replaced with a heating mantle and the reaction mixture is heated at reflux overnight. Then, the reaction solution is cooled down to 0° C. (the heating mantle was replaced with an ice-bath), and the mixture is diluted with 500 ml diethyl ether. The reaction is worked up by adding 160 ml of 15% wt. of an aqueous NaOH solution drop-wise (via an addition funnel) with vigorous stirring. The starting gray reaction solution changes to a colorless liquid with a white powdery precipitate. The solution mixture is filtered and the filtrate is dried over anhydrous magnesium sulfate. Filtration and concentration of the filtrate gives 106 gm (94% yield) of the desired amine 1-[1-(4-chloro-phenyl)-cyclopropylmethyl]-pyrrolidine as a pale yellow oily substance. The amine is pure as indicated by the clean $^1$H and $^{13}$C-NMR spectral analysis.

The parent amide [1-(4-chloro-phenyl)-cyclopropyl]-pyrrolidin-1-yl-methanone is prepared by reacting pyrrolidine with 1-(4-chloro-phenyl)-cyclopropanecarbonyl chloride. A 2-Liter reaction flask equipped with a mechanical stirrer is charged with 1000 ml of dry benzene, 53.5 gm (0.75 mol.) of pyrrolidine and 76 gm (0.75 mol.) of triethyl amine. To this mixture (at 0° C.), 108 1-(4-chloro-phenyl)-cyclopropanecarbonyl chloride gm (0.502 mol.) of (dissolved 100 ml benzene) is added drop-wise (via an addition funnel). Once the addition is completed, the resulting mixture is allowed to stir at room temperature overnight. The reaction mixture (a biphasic mixture: liquid and tan-colored precipitate) is concentrated on a rotary evaporator at reduced pressure to strip off excess pyrrolidine and the solvent (usually hexane or benzene). The remaining residue is diluted with 750 ml water and extracted with 750 ml chloroform in a separatory funnel. The organic layer is washed twice with 500 ml water and once with brine. Then, the organic layer is dried over anhydrous sodium sulfate, filtered and concentrated on a rotary evaporator at reduced pressure to give 122 gm (0.49 mol, 97% yield) of the amide as a tan-colored solid substance.

The 1-(4-chloro-phenyl)-cyclopropanecarbonyl chloride used in the synthesis of the amide is synthesized by treatment of the parent acid 1-(4-chloro-phenyl)-cyclopropanecarboxylic acid with thionyl chloride (SOCl$_2$) as described below. To 200 gms of thionyl chloride and 200 ml dichloromethane in a 3-necked reaction flask, equipped with a mechanical stirrer and a reflux condenser, 100 gm (0.51 mol.) of the 1-(4-chloro-phenyl)-cyclopropanecarboxylic acid is added in small increments (5 gm at a time) over 15 minutes period. Once all the acid is added, the reaction mixture is then heated at reflux. The reaction vessel is equipped with a trap (filled with water) to collect and trap the acidic gaseous byproducts, and used in monitoring the reaction. The reaction is usually done once the evolution of the gaseous byproducts is ceased. The reaction mixture is then cooled down and concentrated on a rotary evaporator at reduced pressure to remove excess thionyl chloride and dichloromethane. The reaction yields 109 gm (98%) of the desired 1-(4-chloro-phenyl)-cyclopropanecarbonyl chloride as reddish viscous oil.

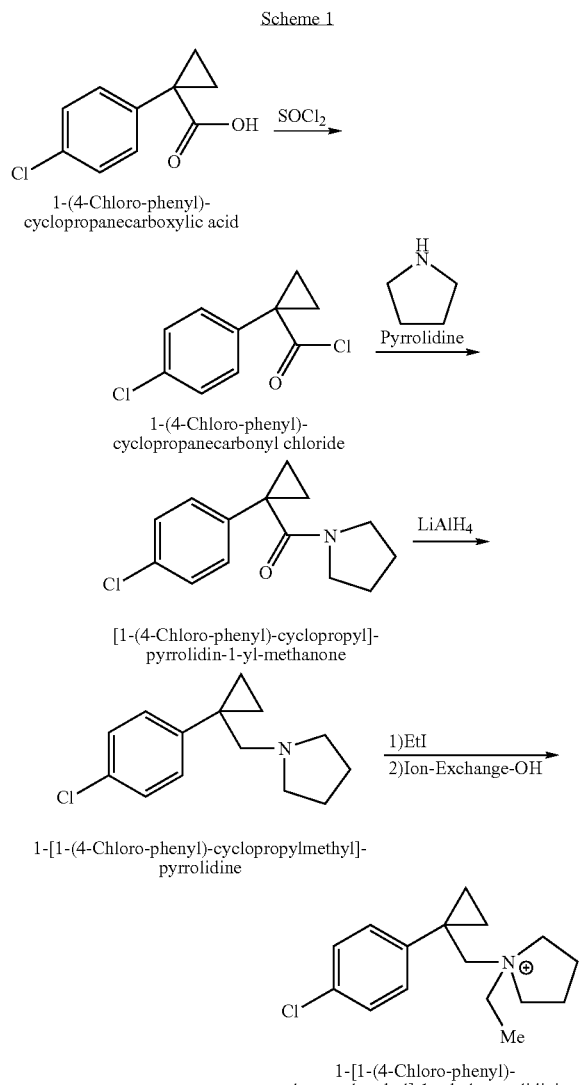

Example 2

Synthesis of SDA 1-ethyl-1-(1-phenyl-cyclopropyl-methyl)-pyrrolidinium cation

SDA 1-ethyl-1-(1-phenyl-cyclopropylmethyl)-pyrrolidinium cation is synthesized using the synthesis procedure of Example 1, except that the synthesis starts from 1-phenyl-cyclopropanecarbonyl chloride and pyrrolidine.

Example 3

Synthesis of SSZ-65

A 23 cc Teflon liner is charged with 5.4 gm of 0.6M aqueous solution of 1-ethyl-1-(1-phenyl-cyclopropylm-ethyl)-pyrrolidinium hydroxide (3 mmol SDA), 1.2 gm of 1M aqueous solution of NaOH (1.2 mmol NaOH) and 5.4 gm of de-ionized water. To this mixture, 0.06 gm of sodium borate decahydrate (0.157 mmol of $Na_2B_4O_7 \cdot 10H_2O$; ~0.315 mmol $B_2O_3$) is added and stirred until completely dissolved. Then, 0.9 gm of CAB-O-SIL® M-5 fumed silica (~14.7 mmol $SiO_2$) is added to the solution and the mixture is thoroughly stirred. The resulting gel is capped off and placed in a Parr bomb steel reactor and heated in an oven at 160° C. while rotating at 43 rpm. The reaction is monitored by checking the gel's pH, and by looking for crystal formation using Scanning Electron Microscopy (SEM). The reaction is usually complete after heating 9–12 days at the conditions described above. Once the crystallization is completed, the starting reaction gel turns to a mixture comprised of a clear liquid and powdery precipitate. The mixture is filtered through a fritted-glass funnel. The collected solids are thoroughly washed with water and, then, rinsed with acetone (10 ml) to remove any organic residues. The solids are allowed to air-dry overnight and, then, dried in an oven at 120° C. for 1 hour. The reaction affords 0.85 gram of a very fine powder. SEM shows the presence of only one crystalline phase. The as-synthesized product is determined by powder XRD data analysis to be SSZ-65 and has the following XRD lines:

| 2 Theta[a] | d-spacing (Angstroms) | Relative Intensity (%) |
| --- | --- | --- |
| 5.98 | 14.78 | 10.1 |
| 6.94 | 12.74 | 26.7 |
| 9.18 | 9.63 | 22.7 |
| 10.44 | 8.47 | 9.4 |
| 12.10 | 7.32 | 9.6 |
| 12.56 | 7.05 | 8.3 |
| 16.00 | 5.54 | 14.2 |
| 17.48 | 5.07 | 25.8 |
| 18.14 | 4.89 | 6.3 |
| 21.02 | 4.23 | 100.0 |
| 21.88 | 4.06 | 47.8 |
| 22.20 | 4.00 | 27.0 |
| 23.02 | 3.86 | 36.8 |
| 23.54 | 3.78 | 8.7 |
| 24.34 | 3.66 | 14.9 |
| 26.06 | 3.42 | 9.9 |
| 26.56 | 3.36 | 21.9 |
| 27.52 | 3.24 | 6.6 |
| 28.00 | 3.19 | 27.0 |
| 28.88 | 3.09 | 8.2 |
| 30.12 | 2.97 | 5.2 |
| 30.54 | 2.93 | 8.7 |
| 31.42 | 2.85 | 15.1 |

Example 4

Seeded Synthesis of Borosilicate SSZ-65

The synthesis of borosilicate SSZ-65 (B-SSZ-65) described in Example 3 above is repeated with the exception of adding 0.04 gm of SSZ-65 as seeds to speed up the crystallization process. The reaction conditions are exactly the same as for the previous example. The crystallization is complete in four days and affords 0.9 gm of B-SSZ-65.

Example 5

Synthesis of Aluminosilicate SSZ-65

A 23 cc Teflon liner is charged with 4 gm of 0.6M aqueous solution of 1-ethyl-1-(1-phenyl-cyclopropylmethyl)-pyrrolidinium hydroxide (2.25 mmol SDA), 1.5 gm of 1M aqueous solution of NaOH (1.5 mmol NaOH) and 2 gm of de-ionized water. To this mixture, 0.25 gm of Na—Y zeolite (Union Carbide's LZY-52; $SiO_2/Al_2O_3$=5) is added and stirred until completely dissolved. Then, 0.85 gm of CAB-O-SIL® M-5 fumed silica (~14. mmol $SiO_2$) is added to the solution and the mixture is thoroughly stirred. The resulting gel is capped off and placed in a Parr bomb steel reactor and heated in an oven at 160° C. while rotating at 43 rpm. The reaction is monitored by checking the gel's pH (increase in the pH usually results from condensation of the silicate species during crystallization, and decrease in pH often indicates decomposition of the SDA), and by checking for crystal formation by scanning electron microscopy. The reaction is usually complete after heating for 12 days at the conditions described above. Once the crystallization is completed, the starting reaction gel turns to a mixture comprised of a liquid and powdery precipitate. The mixture is filtered through a fritted-glass funnel. The collected solids are thoroughly washed with water and, then, rinsed with acetone (10 ml) to remove any organic residues. The solids are allowed to air-dry overnight and, then, dried in an oven at 120° C. for 1 hour. The reaction affords 0.8 gram of SSZ-65.

Examples 6–15

Syntheses of SSZ-65 at Varying $SiO_2/B_2O_3$ Ratios

SSZ-65 is synthesized at varying $SiO_2/B_2O_3$ mole ratios in the starting synthesis gel. This is accomplished using the synthetic conditions described in Example 3 keeping everything the same while changing the $SiO_2/B_2O_3$ mole ratios in the starting gel. This is done by keeping the amount of CAB-O-SIL® M-5 (98% $SiO_2$ and 2% $H_2O$) the same while varying the amount of sodium borate in each synthesis. Consequently, varying the amount of sodium borate leads to varying the $SiO_2/Na$ mole ratios in the starting gels. Table 1 below shows the results of a number of syntheses with varying $SiO_2/B_2O_3$ in the starting synthesis gel.

TABLE 1

| Example No. | $SiO_2/B_2O_3$ | $SiO_2/Na$ | Crystallization Time(days) | Products |
|---|---|---|---|---|
| 6 | 140 | 13.3 | 15 | SSZ-65 |
| 7 | 93 | 12.7 | 12 | SSZ-65 |
| 8 | 70 | 12.1 | 12 | SSZ-65 |
| 9 | 56 | 11.6 | 12 | SSZ-65 |
| 10 | 47 | 11.2 | 12 | SSZ-65 |
| 11 | 40 | 10.7 | 12 | SSZ-65 |
| 12 | 31 | 10 | 12 | SSZ-65 |
| 13 | 23 | 9 | 12 | SSZ-65 |
| 14 | 19 | 8.2 | 6 | SSZ-65 |
| 15 | 14 | 7.1 | 6 | SSZ-65 |

$^-OH/SiO_2$ = 0.28, $R^+/SiO_2$ = 0.2, $H_2O/SiO_2$ = 44
($R^+$ = organic cation (SDA))

Example 16

Calcination of SSZ-65

SSZ-65 as synthesized in Example 3 is calcined to remove the structure directing agent (SDA) as described below. A thin bed of SSZ-65 in a calcination dish is heated in a muffle furnace from room temperature to 120° C. at a rate of 1° C./minute and held for 2 hours. Then, the temperature is ramped up to 540° C. at a rate of 1° C./minute and held for 5 hours. The temperature is ramped up again at 1° C./minute to 595° C. and held there for 5 hours. A 50/50 mixture of air and nitrogen passes through the muffle furnace at a rate of 20 standard cubic feet (0.57 standard cubic meters) per minute during the calcination process. The calcined SSZ-65 has the following XRD lines:

| 2 Theta[a] | d-spacing (Angstroms) | Relative Intensity (%) |
|---|---|---|
| 6.08 | 14.54 | 37.7 |
| 6.98 | 12.66 | 82.8 |
| 9.28 | 9.53 | 50.7 |
| 10.52 | 8.41 | 16.4 |
| 12.14 | 7.29 | 14.3 |
| 12.64 | 7.00 | 6.2 |
| 14.06 | 6.30 | 5.0 |
| 15.26 | 5.81 | 8.1 |
| 16.10 | 5.50 | 17.5 |
| 17.58 | 5.04 | 28.2 |
| 18.30 | 4.85 | 5.3 |
| 21.14 | 4.20 | 100.0 |
| 21.98 | 4.04 | 47.8 |
| 22.26 | 3.99 | 19.6 |
| 23.14 | 3.84 | 28.3 |
| 23.66 | 3.76 | 7.7 |
| 24.50 | 3.63 | 13.1 |
| 26.24 | 3.40 | 8.6 |
| 26.68 | 3.34 | 20.4 |
| 28.10 | 3.18 | 26.8 |
| 28.96 | 3.08 | 7.0 |
| 30.24 | 2.96 | 5.6 |
| 30.68 | 2.91 | 9.7 |
| 31.54 | 2.84 | 14.6 |

Example 17

Conversion of Borosilicate-SSZ-65 to Aluminosilicate SSZ-65

The calcined version of borosilicate SSZ-65 (as synthesized in Example 3 and calcined in Example 16) is easily converted to the aluminosilicate SSZ-65 version by suspending borosilicate SSZ-65 in 1M solution of aluminum nitrate nonahydrate (15 ml of 1M $Al(NO_3)_3.9H_2O$ soln./1 gm SSZ-65). The suspension is heated at reflux overnight. The resulting mixture is then filtered and the collected solids are thoroughly rinsed with de-ionized water and air-dried overnight. The solids are further dried in an oven at 120° C. for 2 hours.

Example 18

Ammonium-Ion Exchange of SSZ-65

The $Na^+$ form of SSZ-65 (prepared as in Example 3 or as in Example 5 and calcined as in Example 16) is converted to $NH_4^+$-SSZ-65 form by heating the material in an aqueous solution of $NH_4NO_3$ (typically 1 gm $NH_4NO_3$/1 gm SSZ-65 in 20 ml $H_2O$) at 90° C. for 2–3 hours. The mixture is then filtered and the obtained $NH_4$-exchanged-product is washed with de-ionized water and dried. The $NH_4^+$ form of SSZ-65 can be converted to the $H^+$ form by calcination (as described in Example 16) to 540° C.

Example 19

Argon Adsorption Analysis

SSZ-65 has a micropore volume of 0.16 cc/gm based on argon adsorption isotherm at 87.5° K (−186° C.) recorded on ASAP 2010 equipment from Micromerities. The sample is first degassed at 400° C. for 16 hours prior to argon adsorption. The low-pressure dose is 6.00 cm³/g (STP). A maximum of one hour equilibration time per dose is used and the total run time is 35 hours. The argon adsorption isotherm is analyzed using the density function theory (DFT) formalism and parameters developed for activated carbon slits by Olivier (*Porous Mater.* 1995, 2, 9) using the Saito Foley adaptation of the Horvarth-Kawazoe formalism (*Microporous Materials,* 1995, 3, 531) and the conventional t-plot method (*J. Catalysis,* 1965, 4, 319).

Example 20

Constraint Index

The hydrogen form of SSZ-65 of Example 3 (after treatment according to Examples 16, 17 and 18) is pelletized at 3 KPSI, crushed and granulated to 20–40 mesh. A 0.6 gram sample of the granulated material is calcined in air at 540° C. for 4 hours and cooled in a desiccator to ensure dryness. Then, 0.5 gram is packed into a ⅜ inch stainless steel tube with alundum on both sides of the molecular sieve bed. A Lindburg furnace is used to heat the reactor tube. Helium is introduced into the reactor tube at 10 cc/min. and at atmospheric pressure. The reactor is heated to about 315° C., and a 50/50 feed of n-hexane and 3-methylpentane is introduced into the reactor at a rate of 8 μl/min. The feed is delivered by a Brownlee pump. Direct sampling into a GC begins after 10 minutes of feed introduction. The Constraint Index (CI) value is calculated from the GC data using methods known in the art. SSZ-65 has a CI of 0.67 and a conversion of 92% after 20 minutes on stream. The material fouls rapidly and at 218 minutes the CI is 0.3 and the conversion is 15.7%. The data suggests a large pore zeolite with perhaps large cavities.

Example 21

Hydrocracking of n-Hexadecane

A 1 gm sample of SSZ-65 (prepared as in Example 3 and treated as in Examples 16, 17 and 18) is suspended in 10 gm de-ionized water. To this suspension, a solution of Pd(NH$_3$)$_4$(NO$_3$)$_2$ at a concentration which would provide 0.5 wt. % Pd with respect to the dry weight of the molecular sieve sample is added. The pH of the solution is adjusted to pH of ~9 by a drop-wise addition of dilute ammonium hydroxide solution. The mixture is then heated in an oven at 75° C. for 48 hours. The mixture is then filtered through a glass frit, washed with de-ionized water, and air-dried. The collected Pd-SSZ-65 sample is slowly calcined up to 482° C. in air and held there for three hours.

The calcined Pd/SSZ-65 catalyst is pelletized in a Carver Press and granulated to yield particles with a 20/40 mesh size. Sized catalyst (0.5 g) is packed into a ¼ inch OD tubing reactor in a micro unit for n-hexadecane hydroconversion. The table below gives the run conditions and the products data for the hydrocracking test on n-hexadecane.

After the catalyst is tested with n-hexadecane, it is titrated using a solution of butylamine in hexane. The temperature is increased and the conversion and product data evaluated again under titrated conditions. The results shown in the table below show that SSZ-65 is effective as a hydrocracking catalyst.

| | |
|---|---|
| Temperature | 260° C. (550° F.) |
| Time-on-Stream (hrs.) | 342.4–343.4 |
| WHSV | 1.55 |
| PSIG | 1200 |
| Titrated? | Yes |
| n-16, % Conversion | 96.9 |
| Hydrocracking Conv. | 47.9 |
| Isomerization Selectivity, % | 50.5 |
| Cracking Selectivity, % | 49.5 |
| C$_{4-}$, % | 2.7 |
| C$_5$/C$_4$ | 16.9 |
| C$_5$+C$_6$/C$_5$, % | 16.74 |
| DMB/MP | 0.06 |
| C$_4$–C$_{13}$ i/n | 3.83 |
| C$_7$–C$_{13}$ yield | 38.35 |

Example 22

Synthesis of SSZ-65

SSZ-65 is synthesized in a manner similar to that of Example 3 using a 1-[1-(4-chlorophenyl)-cyclopropylmethyl]-1-ethyl-pyrrolidinium cation as the SDA.

What is claimed is:

1. A process for converting hydrocarbons comprising contacting a hydrocarbonaceous feed at hydrocarbon converting conditions with a catalyst comprising a zeolite having a mole ratio greater than about 15 of (1) an oxide of a first tetravalent element to (2) an oxide of a trivalent element, pentavalent element, second tetravalent element which is different from said first tetravalent element or mixture thereof and having, after calcination, the X-ray diffraction lines of Table II.

2. The process of claim 1 wherein the zeolite is predominantly in the hydrogen form.

3. The process of claim 1 wherein the zeolite is substantially free of acidity.

4. The process of claim 1 wherein the process is a hydrocracking process comprising contacting the catalyst with a hydrocarbon feedstock under hydrocracking conditions.

5. The process of claim 4 wherein the zeolite is predominantly in the hydrogen form.

6. The process of claim 1 wherein the process is a dewaxing process comprising contacting the catalyst with a hydrocarbon feedstock under dewaxing conditions.

7. The process of claim 6 wherein the zeolite is predominantly in the hydrogen form.

8. The process of claim 1 wherein the process is a process for improving the viscosity index of a dewaxed product of waxy hydrocarbon feeds comprising contacting the catalyst with a waxy hydrocarbon feed under isomerization dewaxing conditions.

9. The process of claim 8 wherein the zeolite is predominantly in the hydrogen form.

10. The process of claim 1 wherein the process is a process for producing a C$_{20+}$ lube oil from a C$_{20+}$ olefin feed comprising isomerizing said olefin feed under isomerization conditions over the catalyst.

11. The process of claim 10 wherein the zeolite is predominantly in the hydrogen form.

12. The process of claim 10 wherein the catalyst further comprises at least one Group VIII metal.

13. The process of claim 1 wherein the process is a process for catalytically dewaxing a hydrocarbon oil feedstock boiling above about 350° F. (177° C.) and containing straight chain and slightly branched chain hydrocarbons comprising contacting said hydrocarbon oil feedstock in the presence of added hydrogen gas at a hydrogen pressure of about 15–3000 psi (0.103–20.7 MPa) under dewaxing conditions with the catalyst.

14. The process of claim 13 wherein the zeolite is predominantly in the hydrogen form.

15. The process of claim 13 wherein the catalyst further comprises at least one Group VIII metal.

16. The process of claim 13 wherein said catalyst comprises a layered catalyst comprising a first layer comprising the zeolite and at least one Group VIII metal, and a second layer comprising an aluminosilicate zeolite which is more shape selective than the zeolite of said first layer.

17. The process of claim 1 wherein the process is a process for preparing a lubricating oil which comprises:
hydrocracking in a hydrocracking zone a hydrocarbonaceous feedstock to obtain an effluent comprising a hydrocracked oil; and
catalytically dewaxing said effluent comprising hydrocracked oil at a temperature of at least about 400° F. (204° C.) and at a pressure of from about 15 psig to about 3000 psig (0.103 to 20.7 MPa gauge) in the presence of added hydrogen gas with the catalyst.

18. The process of claim 17 wherein the zeolite is predominantly in the hydrogen form.

19. The process of claim 17 wherein the catalyst further comprises at least one Group VIII metal.

20. The process of claim 1 wherein the process is a process for isomerization dewaxing a raffinate comprising contacting said raffinate in the presence of added hydrogen under isomerization dewaxing conditions with the catalyst.

21. The process of claim 20 wherein the zeolite is predominantly in the hydrogen form.

22. The process of claim 20 wherein the catalyst further comprises at least one Group VIII metal.

23. The process of claim 20 wherein the raffinate is bright stock.

24. The process of claim 1 wherein the process is a process for increasing the octane of a hydrocarbon feedstock to produce a product having an increased aromatics content comprising contacting a hydrocarbonaceous feedstock which comprises normal and slightly branched hydrocarbons having a boiling range above about 40° C. and less than about 200° C. under aromatic conversion conditions with the catalyst.

25. The process of claim 24 wherein the zeolite is substantially free of acid.

26. The process of claim 24 wherein the zeolite contains a Group VIII metal component.

27. The process of claim 1 wherein the process is a catalytic cracking process comprising contacting a hydrocarbon feedstock in a reaction zone under catalytic cracking conditions in the absence of added hydrogen with the catalyst.

28. The process of claim 27 wherein the zeolite is predominantly in the hydrogen form.

29. The process of claim 27 wherein the catalyst additionally comprises a large pore crystalline cracking component.

30. The process of claim 1 wherein the process is an isomerization process for isomerizing $C_4$ to $C_7$ hydrocarbons, comprising contacting a feed having normal and slightly branched $C_4$ to $C_7$ hydrocarbons under isomerizing conditions with the catalyst.

31. The process of claim 30 wherein the zeolite is predominantly in the hydrogen form.

32. The process of claim 30 wherein the zeolite has been impregnated with at least one Group VIII metal.

33. The process of claim 30 wherein the catalyst has been calcined in a steam/air mixture at an elevated temperature after impregnation of the Group VIII metal.

34. The process of claim 32 wherein the Group VIII metal is platinum.

35. The process of claim 1 wherein the process is a process for alkylating an aromatic hydrocarbon which comprises contacting under alkylation conditions at least a molar excess of an aromatic hydrocarbon with a $C_2$ to $C_{20}$ olefin under at least partial liquid phase conditions and in the presence of the catalyst.

36. The process of claim 35 wherein the zeolite is predominantly in the hydrogen form.

37. The process of claim 35 wherein the olefin is a $C_2$ to $C_4$ olefin.

38. The process of claim 37 wherein the aromatic hydrocarbon and olefin are present in a molar ratio of about 4:1 to about 20:1, respectively.

39. The process of claim 37 wherein the aromatic hydrocarbon is selected from the group consisting of benzene, toluene, ethylbenzene, xylene, naphthalene, naphthalene derivatives, dimethylnaphthalene or mixtures thereof.

40. The process of claim 1 wherein the process is a process for transalkylating an aromatic hydrocarbon which comprises contacting under transalkylating conditions an aromatic hydrocarbon with a polyalkyl aromatic hydrocarbon under at least partial liquid phase conditions and in the presence of the catalyst.

41. The process of claim 40 wherein the zeolite is predominantly in the hydrogen form.

42. The process of claim 40 wherein the aromatic hydrocarbon and the polyalkyl aromatic hydrocarbon are present in a molar ratio of from about 1:1 to about 25:1, respectively.

43. The process of claim 40 wherein the aromatic hydrocarbon is selected from the group consisting of benzene, toluene, ethylbenzene, xylene, or mixtures thereof.

44. The process of claim 40 wherein the polyalkyl aromatic hydrocarbon is a dialkylbenzene.

45. The process of claim 1 wherein the process is a process to convert paraffins to aromatics which comprises contacting paraffins under conditions which cause paraffins to convert to aromatics with a catalyst comprising the zeolite and gallium, zinc, or a compound of gallium or zinc.

46. The process of claim 1 wherein the process is a process for isomerizing olefins comprising contacting said olefin under conditions which cause isomerization of the olefin with the catalyst.

47. The process of claim 1 wherein the process is a process for isomerizing an isomerization feed comprising an aromatic $C_8$ stream of xylene isomers or mixtures of xylene isomers and ethylbenzene, wherein a more nearly equilibrium ratio of ortho-, meta and para-xylenes is obtained, said process comprising contacting said feed under isomerization conditions with the catalyst.

48. The process of claim 1 wherein the process is a process for oligomerizing olefins comprising contacting an olefin feed under oligomerization conditions with the catalyst.

49. A process for converting oxygenated hydrocarbons comprising contacting said oxygenated hydrocarbon under conditions to produce liquid products with a catalyst comprising a zeolite having a mole ratio greater than about 15 of an oxide of a first tetravalent element to an oxide of a second tetravalent element which is different from said first tetravalent element, trivalent element, pentavalent element or mixture thereof and having, after calcination, the X-ray diffraction lines of Table II.

50. The process of claim 49 wherein the oxygenated hydrocarbon is a lower alcohol.

51. The process of claim 50 wherein the lower alcohol is methanol.

52. The process of claim 1 wherein the process is a process for the production of higher molecular weight hydrocarbons from lower molecular weight hydrocarbons comprising the steps of:
(a) introducing into a reaction zone a lower molecular weight hydrocarbon containing gas and contacting said gas in said zone under $C_{2+}$ hydrocarbon synthesis conditions with the catalyst and a metal or metal compound capable of converting the lower molecular weight hydrocarbon to a higher molecular weight hydrocarbon; and
(b) withdrawing from said reaction zone a higher molecular weight hydrocarbon-containing stream.

53. The process of claim 52 wherein the metal or metal compound comprises a lanthanide or actinide metal or metal compound.

54. The process of claim 52 wherein the lower molecular weight hydrocarbon is methane.

* * * * *